United States Patent [19]

Flachslaender et al.

[11] Patent Number: 5,740,001
[45] Date of Patent: Apr. 14, 1998

[54] PATIENT MONITORING MODULE

[75] Inventors: Erwin Flachslaender, Calw; Matthias Muehle, Stuttgart; Wolfgang Kehrer, Boeblingen, all of Germany

[73] Assignee: Hewlett-Packard Company, Palo Alto, Calif.

[21] Appl. No.: 669,202

[22] Filed: Jun. 24, 1996

[30] Foreign Application Priority Data

Jul. 27, 1995 [EP] European Pat. Off. ............... 95111807

[51] Int. Cl.$^6$ ............................................... H02H 3/20
[52] U.S. Cl. ................. 361/91; 361/746; 361/793; 361/800
[58] Field of Search ................. 361/91, 728, 733, 361/736, 752, 758, 829, 742, 777, 790, 803–804, 739, 746, 750, 780, 793–795, 800, 816, 720–721, 735, 748; 174/52.1, 50.59, 50, 50.5, 50.51, 50.52; 379/416

[56] References Cited

U.S. PATENT DOCUMENTS

| | | | |
|---|---|---|---|
| 2,995,686 | 8/1961 | Selvin | 361/733 |
| 4,399,487 | 8/1983 | Neumann | 361/736 |
| 4,688,579 | 8/1987 | Inahara | 128/695 |
| 4,715,385 | 12/1987 | Cudahy et al. | 128/710 |
| 4,742,831 | 5/1988 | Silvian | 128/710 |
| 5,019,945 | 5/1991 | Smolley | 361/803 |
| 5,373,104 | 12/1994 | Brauer | 174/52.1 |
| 5,504,940 | 4/1996 | Hahs, Jr. et al. | 455/38.1 |
| 5,513,077 | 4/1996 | Stribel | 361/794 |
| 5,544,017 | 8/1996 | Beilin et al. | 361/790 |

OTHER PUBLICATIONS

Medical & Biological Engineering & Computing, vol. 26, No. 4, Jul. 1988, pp. 397–403, T. Takaki, "EEG enhancement during electrosurgery using an optical fibre".

Proceedings of the IEEE 1988 Custom Integrated Circuits Conference, 16 May 1988, pp. 941–946, G. McGlinchey et al., "A Programmable Medical Data Acquisition System Chip".

European Search Report, EP 95 11 1807, 20 Dec. 1995.

*Primary Examiner*—Jeffrey A. Gaffin
*Assistant Examiner*—Michael J. Sherry

[57] ABSTRACT

A patient monitoring/signal processing module with increased electrical isolation is disclosed. The combination of an inner isolation piece and an isolation film provide signal isolation and electrical over-voltage protection between a lower, isolated portion of the unit defined by a lower housing and the isolation piece and an upper, non-isolated portion of the unit, defined by an upper housing and the isolation piece, increasing the module's ability to survive an over-voltage condition without damage to itself or to the patient to whom it is coupled. The combination of the isolation film and the isolation piece results in a much thinner module than would otherwise have been necessary to achieve the same levels of signal and electrical isolation.

12 Claims, 5 Drawing Sheets

PATIENT MONITORING MODULE

FIELD OF THE INVENTION

This invention is in the field of medical instrumentation and patient monitoring systems. In particular, the present invention relates to miniaturized patient monitoring systems.

BACKGROUND OF THE INVENTION

Monitoring systems for critically and acutely ill patients are known. Such units can monitor and continuously display patient vital signs including heart rate, blood pressure, measured both invasively and non-invasively, temperature, cardiac output, blood oxygen saturation and other signs. Known patient monitoring systems function well, but several operational difficulties are known.

Many known systems are large, independent units, which process received data internally and display it on a connected monitor. The size of such units makes them difficult to move. When patients are moved from their room to an operating theater or examining area, they must be disconnected from the monitoring system in their present location and then reconnected to another monitoring system in the new location. This process of connecting and disconnecting the patient is time consuming and results in periods of time when the patient is not connected to a system and is consequently not monitored. The possibility of connecting the patient incorrectly also exists.

Designers of patient monitoring systems have sought to reduce the size of their systems to facilitate transportation. One system resulting from these efforts is disclosed in U.S. Pat. No. 4,715,385, which describes a monitoring system with a data acquisition and processing module and a bedside display unit and/or a portable display unit. The portable display unit accompanies the patient during transport. It is also possible to connect both display units simultaneously so that no data is lost during a patient transfer.

The data acquisition and processing modules receive signals generated by sensors attached to the patient and perform initial signal processing. Typically, they lack large storage memories or displays. Each of these modules must be coupled in turn to a larger processing unit with a display. The advantages of this type of system are that the patient can be quickly connected and disconnected from the module without much disturbance, and a large central processing and display unit can be used with many independent signal processing modules.

Although this approach offers many benefits, collection of many types of signals and processing them in a small module present many challenges. Analog and digital signals may need to be electrically isolated from one another. To avoid damage to the module and possible injury to the patient, a high degree of electrical isolation from both the power supply and static electricity sources must be achieved. Unfortunately, signal and electrical isolation is difficult to achieve in a small signal processing module.

What is needed is a miniaturized patient data collection/data processing module that can monitor and collect many different vital signs from the patient simultaneously, process those signals without mutual interference and maintain a high degree of electrical isolation from both the larger monitoring system and the power supply.

SUMMARY OF THE INVENTION

The present invention, in its first preferred embodiment, comprises a miniaturized patient monitoring/signal processing module which maintains signal isolation to prevent mutual interference and electrical isolation to prevent patient and system damage from electrical over-voltages.

The module comprises a lower housing, upon which a first printed circuit board is mounted. The first printed circuit board has first connectors, which couple to sensors attached to the patient, and an isolation block. An isolation piece overlies the lower housing and the first printed circuit board, the sides of the isolation piece interlocking with the lower housing, and the isolation block extending through a first opening in the isolation piece. A second printed circuit board rests on the top surface of the isolation piece and is coupled to the first printed circuit board through the isolation block. A second connector which rests in an indentation in the isolation piece provides power to the second printed circuit board and allows the module to be coupled to an external monitoring unit with a display. An upper housing overlies the second printed circuit board and interlocks with the sides of the isolation piece. The module has a first compartment, defined by the lower housing and the isolation piece, and a second compartment, defined by the upper housing and the isolation piece, which are electrically isolated from one another.

The isolation block electrically isolates the upper and lower compartments by providing a first transformer half and first electro-optical transceivers coupled to the first printed circuit board. An isolation film overlies the transformers and transceivers, extending at least some distance in front of and behind the transformers and transceivers. A second transformer half and second electro-optical transceivers are placed over the first transformer half and the first electro-optical transceivers and are in optical and magnetic communication therewith. The film permits the upper and lower transformer halves to lie in closer proximity than would otherwise be possible if only air was used as the insulator between the two halves, while the block still provides an electrical over-voltage protection level of at least 16 kV.

The combination of the isolation piece, isolation block and isolation film allows the construction of a medical patient monitoring module with electrical over-voltage protection of at least 16 kV with a final module thickness much less than would otherwise be necessary.

A significant advantage of the present invention is that a thin module can be constructed without any significant increase in manufacturing costs while still achieving adequate levels of electrical over-voltage protection and signal isolation.

DETAILED DESCRIPTION OF THE PREFERRED EMBODIMENTS

Figure 1:
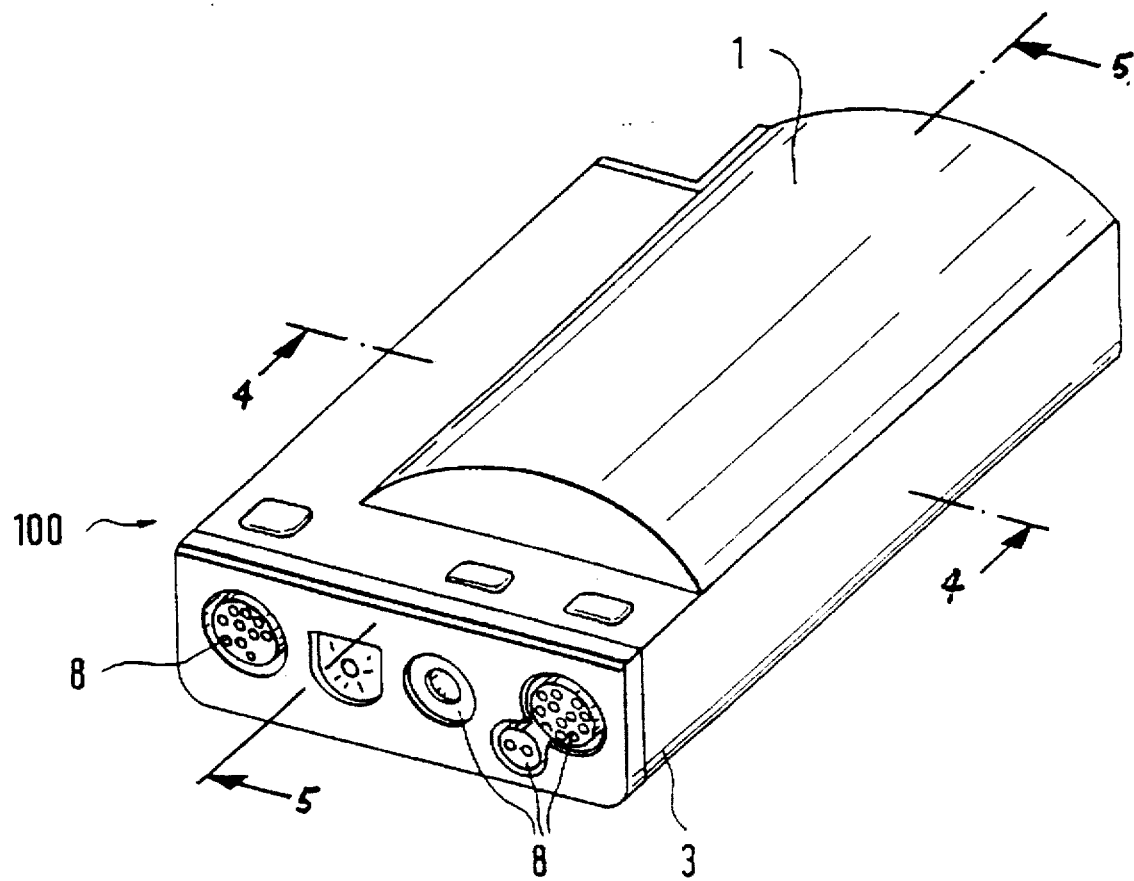
FIG. 1 is a perspective view of the assembled module comprising the preferred embodiment of the present invention.

Patient monitoring module 100 is shown assembled in FIG. 1. It comprises upper housing 1, lower housing 3 and connectors 8 which are coupled to the various sensors attached to the patient. The sensors themselves are not shown. Some of the vital signs that can be monitored are temperature, blood pressure, measured both invasively and non-invasively, ECG, blood oxygen saturation, and blood flow/cardiac output. Certain of these sensed vital signs are delivered to module 100 as analog signals and others are delivered as digital signals. The analog and digital signals require different processing and must be kept from interfering with one another.

Figure 2:
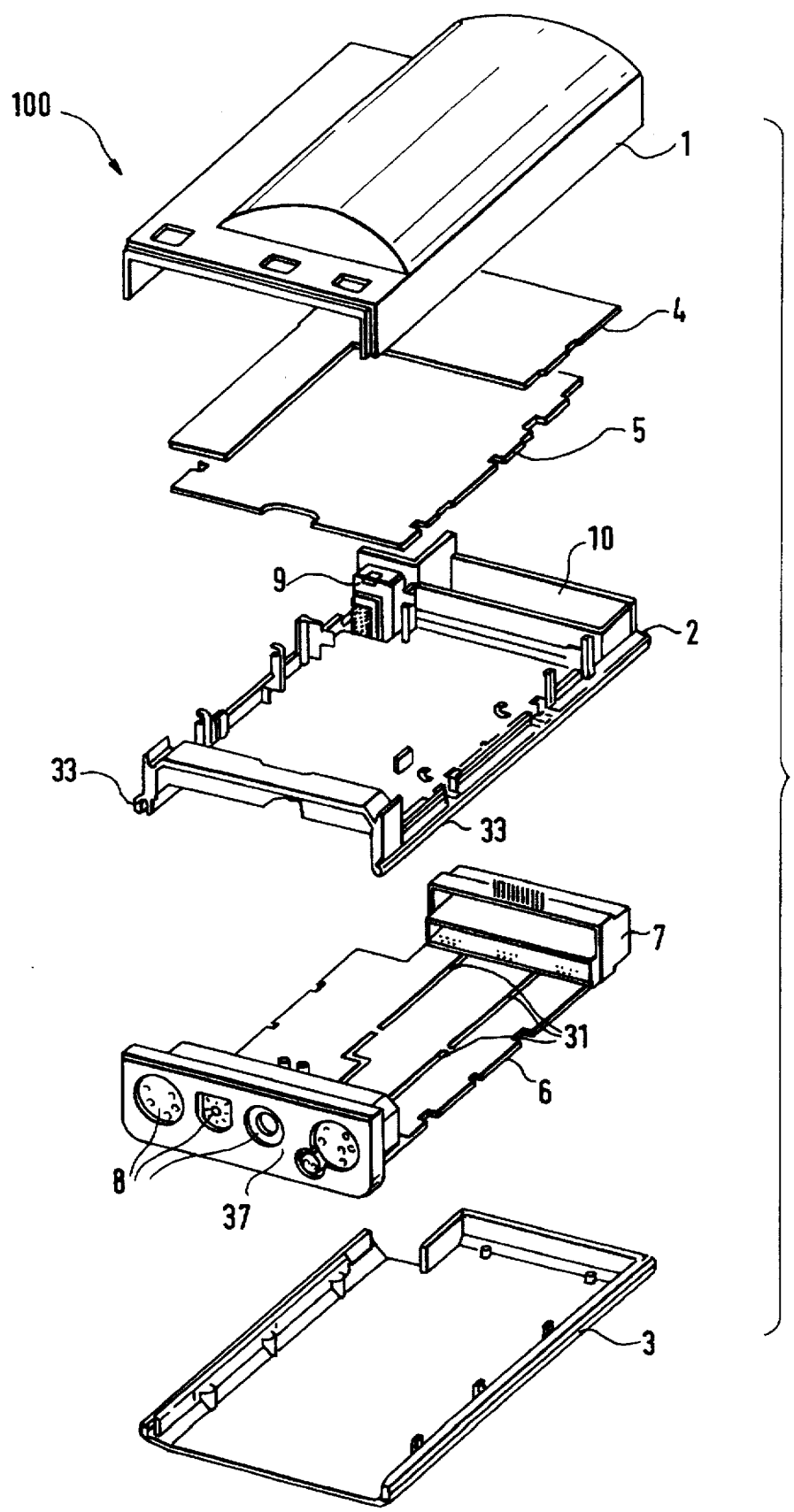
FIG. 2 is an exploded isometric drawing of the module shown in FIG. 1.

The exploded isometric drawing of module 100 shown in FIG. 2 shows the major components of the module and their relationship to one another. Lower printed circuit board 6 is electrically coupled to both connectors 8 and isolation block 7. It is mechanically connected to both the isolation block and front panel 37 into which connectors 8 are inserted. When assembled, lower printed circuit board 6 rests on lower housing 3. Printed circuit board 6 is divided by slots 31 into three separate processing portions, each processing information from one sensor attached to the patient. These channels float at the patient's voltage potential.

Isolation piece 2 lies over lower printed circuit board 6 and is press-fitted into lower housing 3. After assembly, isolation piece 2 covers lower printed circuit board 6 fully and surrounds the rear of connectors 8. Isolation block 7 is inserted through opening 10 in isolation piece 2. Second connector 9 rests within an indentation(not shown) in isolation piece 2, which indentation surrounds the lower sides of connector 9. Connector 9 is coupled to upper printed circuit board 5. In operation, second connector 9 couples module 100 to an external patient monitoring system and provides power to module 100. Upper printed circuit boards 4 and 5 are press fitted into a space on the upper surface of isolation piece 2. Finally, upper housing 1 snaps together with isolation piece 2 to form the completed module 100. Upper housing 1, isolation piece 2, and lower housing 3 are all injection molded from ABS/PC plastic.

Figure 4:
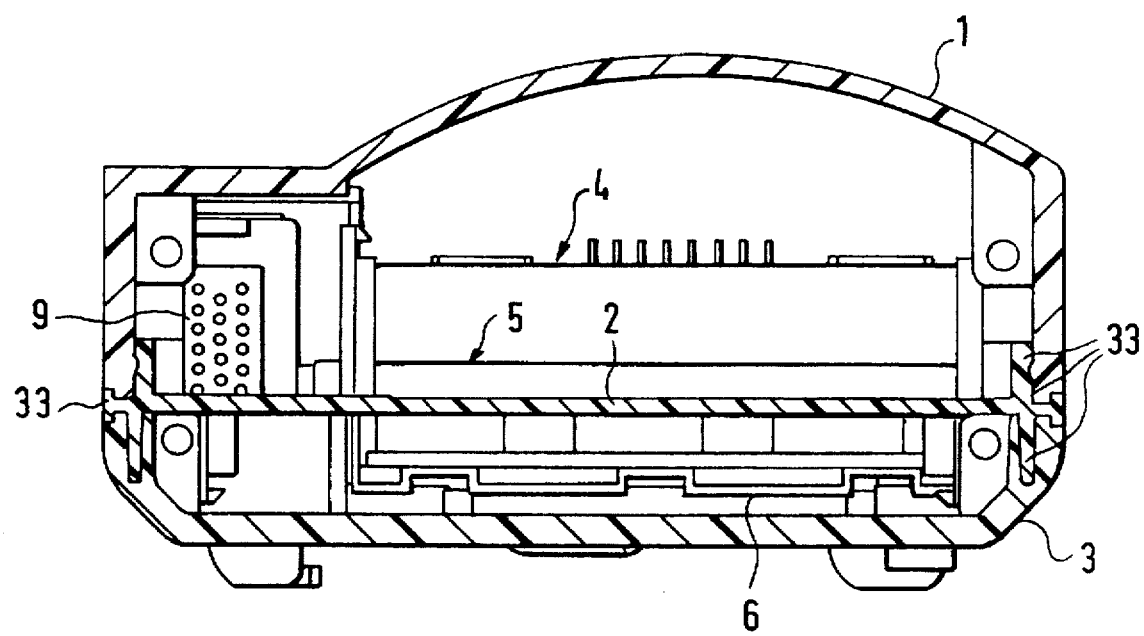
FIG. 4 is a first cross-section of the assembled module, taken along the line 4—4 in FIG. 1.

FIG. 4 illustrates more clearly the positions of the components after the module is assembled and shows how isolation piece 2 electrically and physically separates printed circuit board 6 from printed circuit boards 4 and 5. Side rails 33 of isolation piece 2 interlock with lower housing 3 and upper housing 1. They create a minimum over-voltage pathway along the sides of module 100 that any electrical over-voltage would have to travel before affecting the electronic circuitry of module 100. This pathway maintains electrical isolation along the sides of module 100 at over-voltage levels of at least 16 kV.

The placement of isolation piece 2 between the lower and upper printed circuit boards serves to electrically isolate the boards from one another. As signals must pass from the lower circuit board to the upper circuit boards, it alone cannot insure sufficient electrical and signal isolation. This is especially so as there is an opening 10 in isolation piece 2 (FIG. 2) to allow communication between the two parts of the module.

Figure 3:
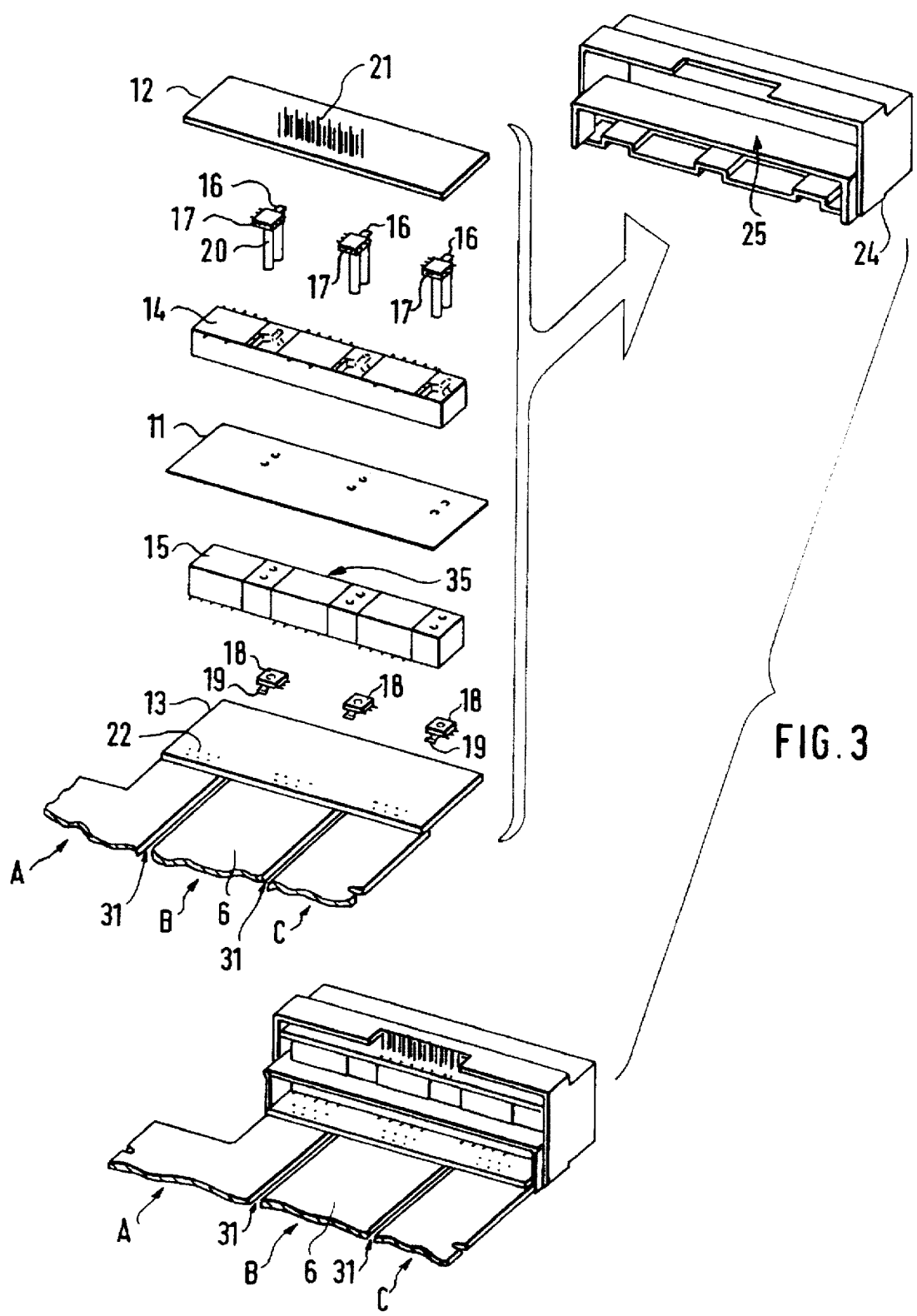
FIG. 3 is a detailed exploded isometric view of the isolation block shown in FIG. 2.

FIG. 3 is a detailed exploded isometric drawing of isolation block 7. Like module 100, the assembled isolation block 7 is comprised of an isolated region and a non-isolated region. Printed circuit board 6 is effectively divided into three channels A, B, and C by slots 31 and provides three different signals to the patient monitoring system. Printed circuit board 6 is coupled to a lower isolation block printed circuit board 13 by means of pin contacts 22. Other types of contacts could be used, as necessary. Optical transceivers 18/19, each typically comprised of at least a light emitting diode and a photo-diode or a photo-transistor are coupled to printed circuit board 13. Lower transformer halves 15 are also coupled to the lower printed circuit board 13. In an embodiment of the present invention, the transformer halves are embedded in an epoxy potting compound and form a rectangular unit. In other embodiments, the transformers are not embedded in such a compound. Although the potting compound increases the electrical isolation of the upper and lower portions of isolation block 7, isolation film 11 alone provides the minimum electric over-voltage protection for block 7.

Isolation film 11 is placed over transformer halves 15 and extends from forward edge 35 of the lower transformer half to at least completely cover the lower transformer half. Its minimum width is 10.5 mm and portions of it may extend both in front of forward edge 35 and behind the lower and upper transformer halves. Film 11 has several holes punched through it, to allow optical communication between optical transceivers 18/19 on lower printed circuit board 13 and upper optical transceivers 16/17 on upper isolation block printed circuit board 12. Like the lower transformer halves, the upper transformer halves may be embedded in an epoxy potting compound. In the first preferred embodiment, light fibers 20 are placed between the transceivers pairs for improved optical communication. Light fibers 20 are glued to upper and lower transceivers 16/17 and 18/19 with a transparent optical glue which insures maximum light transmission between the transceivers. Third connector 21 couples the upper isolation block printed circuit board 12 to upper printed circuit boards 4 and 5. The assembled combination of lower isolation block printed circuit board 13, upper and lower transformer halves 15 and 14, plastic isolation film 11 between the upper and lower transformer halves, optical transceiver pairs 18/19 and 16/17, and upper isolation block printed circuit board 12 is inserted and press-fitted into space 25 in housing 24. A non-transparent potting compound such as epoxy is then injected into the assembly. The completed assembly inserts through opening 10 in isolation piece 2.

In an first alternative embodiment, the non-transparent potting compound is molded with channels therein. These channels align with the transceivers after the isolation block is assembled and are filled with an optically transparent material. In this embodiment, no separate light fibers are needed between the transceivers. In another embodiment, separate light pipes could be mounted on the upper and lower transceivers and aligned across the isolation film. In this embodiment, the isolation film would not have holes punched through it.

The signals which are obtained by channels A, B, and C on lower printed circuit board 6 are converted into optical signals by transceivers 18/19 and transmitted to transceivers 16/17. This provides the necessary signal isolation between the upper and lower portions of module 100. The necessary electrical isolation is obtained by the use of the isolation film 11, the isolation block 7, and the isolation piece 2.

Figure 5:
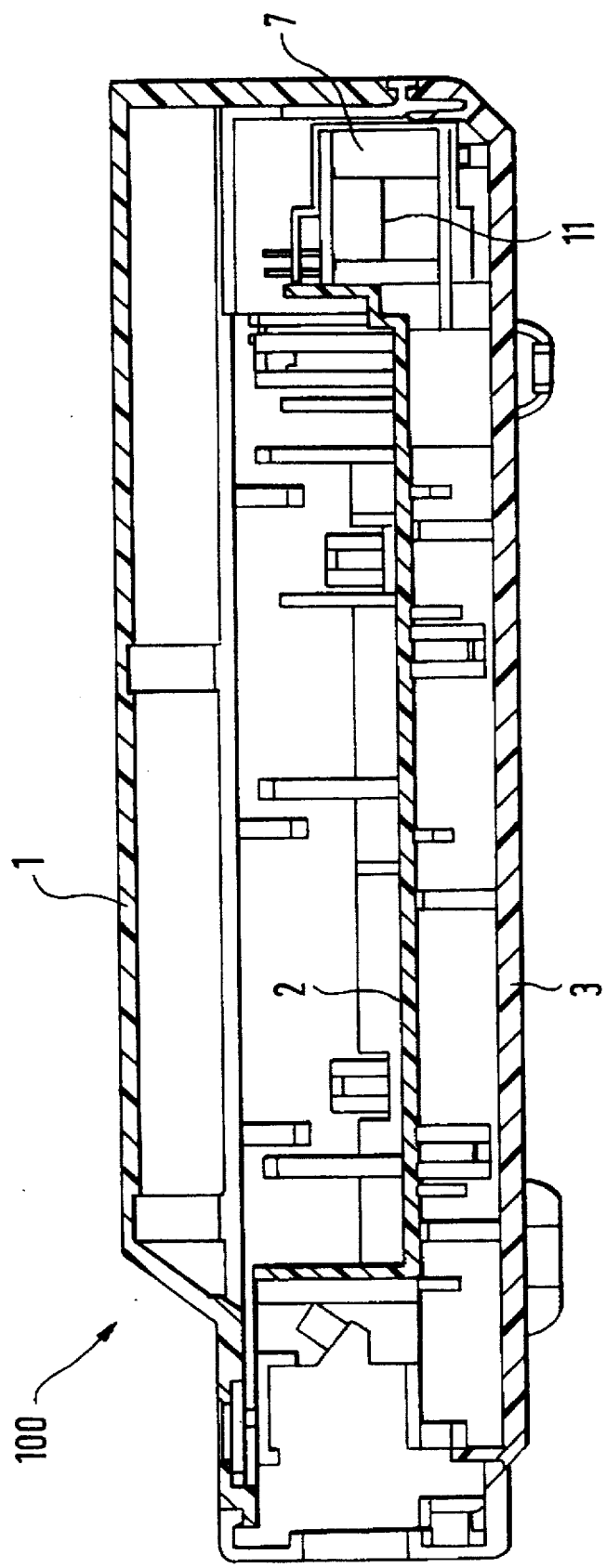
FIG. 5 is a second cross-section of the assembled module taken along line 5—5 in FIG. 1.

A cross-section of module 100, shown in FIG. 5, shows the relative position of the transformers and the isolation film after the entire module has been assembled. The combination of film 11, isolation piece 2, and isolation block 7 creates a pathway of at least 21 millimeters which an over-voltage must travel to reach the printed circuit boards. This distance results in a minimum over-voltage protection level of at least 16 kV. Depending on such factors as relative humidity and particulates, the same arrangement may provide over-voltage protection of up to 21 kV. This level of electrical isolation is much greater than could be achieved by merely maintaining an air gap of equivalent thickness between the upper and lower transformer halves. Although film 11 is pierced in several places to provide for light fibers to couple the optical transceivers together, the epoxy potting compound which surrounds both halves of the transformers as well as the light fibers themselves maintains the requisite level of electrical isolation. Rails 33 of isolation piece 2 (see FIG. 4) also increase the minimum level of electrical over-voltage protection afforded by module 100. In this manner, upper and lower portions of module 100 are effectively hermetically isolated from one another without the necessity of completely surrounding the relative portions with solid, injection molded plastic, permitting a thinner final module than would otherwise be possible.

What is claimed is:

1. A signal processing module with electrical over-voltage protection and signal isolation, comprising:

a lower housing with a first internal surface;

a first printed circuit board with a first connector and an isolation block, the first printed circuit board mounted on the first internal surface of said lower housing;

an isolation piece with an upper surface, mounted over the first printed circuit board and having a first opening for the isolation block and a first indentation for a second connector, the second connector coupling the module to a monitoring system and a power supply;

second printed circuit boards mounting on the upper surface of the isolation piece and coupled to the first printed circuit board by the isolation block, the second connector being coupled to one of the second printed circuit boards; and an upper housing mounting over the second printed circuit boards and mechanically coupled to the lower housing and the isolation piece to form the signal processing module.

2. A signal processing module with an isolation block, the isolation block comprising:

a lower section comprising both signal and power components;

an isolation film overlying the lower section and extending a predefined distance beyond the lower section; and an upper section comprising both signal and power components, overlying the isolation film, the upper section and lower section being in optical and electromagnetic communication with one another through the isolation film, the isolation film preventing direct electrical connection and providing electrical over-voltage protection between the lower section and upper section.

3. The signal processing module of claim 2 wherein the isolation film has at least a first dimension exceeding 10.5 mm and a second dimension exceeding the length of the upper and lower signal and power sections.

4. The signal processing module of claim 1 wherein the isolation piece has side rails which couple with the upper housing and the lower housing when the module is assembled, the side rails forming a channel of at least 21 mm along the sides of the module, over which an electrical over-voltage would flow.

5. The signal processing module of claim 1 wherein the first printed circuit board is divided into three electrically separate channels and the lower and upper signal and power sections have three separate channels.

6. The signal processing module of claim 1, wherein the signal processing module processes patient vital signs.

7. The processing module of claim 6 wherein the first printed circuit board floats at the patient's potential voltage level.

8. The signal processing module of claim 2 wherein the lower section includes a first printed circuit board which is divided into three electrically separate channels, the signal and power components of both the lower section and upper section having three separate channels.

9. The signal processing module of claim 2, wherein the signal processing module processes patient vital signs.

10. The processing module of claim 9 wherein the lower section includes a first printed circuit board which floats at the patient's potential voltage level.

11. The signal processing module of claim 2 wherein the isolation film extends beyond both a front and rear edge of the lower section and upper section.

12. A method for providing signal isolation and over-voltage protection in a signal processing unit, the method comprising the steps of:

dividing the unit into a first signal processing section and a second signal processing section by means of an isolation shield;

creating a first opening in the isolation shield for signal communication and power transmission between the first and second signal processing sections;

transmitting signals between the first and second signal processing sections by means of light signals directed through the first opening;

transmitting power between the first and second signal processing sections by means of an electrical transformer having a first half in the first signal processing section and a second half in the second signal processing section; and placing an isolation film in the optical pathway between the first and second signal processing sections and between the first and second transformer halves, the isolation film permitting optical signal communication, and the isolation film and the isolation shield cooperating to electrically isolate the first and second signal processing sections from one another.

* * * * *